United States Patent
Asami et al.

(10) Patent No.: US 10,494,274 B2
(45) Date of Patent: *Dec. 3, 2019

(54) LIQUID SUBSTANCE STERILIZING METHOD AND APPARATUS

(71) Applicants: NIHON SPINDLE MANUFACTURING CO., LTD., Hyogo (JP); UNIVERSITY OF HYOGO, Hyogo (JP)

(72) Inventors: Keiichi Asami, Hyogo (JP); Keiichiro Onishi, Hyogo (JP); Yoshihiro Oka, Hyogo (JP)

(73) Assignees: NIHON SPINDLE MANUFACTURING CO., LTD., Hyogo (JP); UNIVERSITY OF HYOGO, Hyogo (JP)

(*) Notice: Subject to any disclaimer, the term of this patent is extended or adjusted under 35 U.S.C. 154(b) by 232 days.

This patent is subject to a terminal disclaimer.

(21) Appl. No.: 15/469,215

(22) Filed: Mar. 24, 2017

(65) Prior Publication Data
US 2017/0275187 A1 Sep. 28, 2017

(30) Foreign Application Priority Data
Mar. 28, 2016 (JP) ................. 2016-063092

(51) Int. Cl.
C02F 1/34 (2006.01)
C02F 1/30 (2006.01)
C02F 103/00 (2006.01)

(52) U.S. Cl.
CPC ............. *C02F 1/34* (2013.01); *C02F 1/30* (2013.01); *C02F 2103/008* (2013.01); *C02F 2303/04* (2013.01)

(58) Field of Classification Search
CPC .. C02F 1/30; C02F 1/34; C02F 1/4608; C02F 2103/008; C02F 2303/04; B01D 17/0217; A61L 2202/11
See application file for complete search history.

(56) References Cited

U.S. PATENT DOCUMENTS

| | | | |
|---|---|---|---|
| 2006/0032822 A1* | 2/2006 | Banerjee | C02F 11/12 210/738 |
| 2015/0122741 A1* | 5/2015 | Eckelberry | C12N 13/00 210/704 |

FOREIGN PATENT DOCUMENTS

| | | | |
|---|---|---|---|
| JP | 2008-036555 A | | 2/2008 |
| JP | 2015-003297 A | | 1/2015 |
| JP | 2015003297 A | * | 1/2015 |

OTHER PUBLICATIONS

JP-2015003297-A; English translation. Jan. 2015 country JP. Inventor Yoshino Morihisa. Entire document. (Year: 2015).*

* cited by examiner

*Primary Examiner* — Walter D. Griffin
*Assistant Examiner* — Cameron J Allen
(74) *Attorney, Agent, or Firm* — Michael Best & Friedrich LLP

(57) ABSTRACT

Sterilization of a liquid substance is performed by causing cavitation in the liquid substance by stirring the liquid substance with a rotary blade of a suction stirring pump and generating plasma with a plasma generation mechanism in air bubbles generated in the liquid substance by the cavitation.

10 Claims, 7 Drawing Sheets

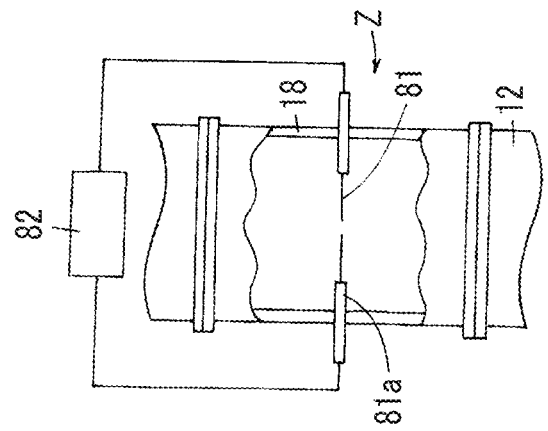
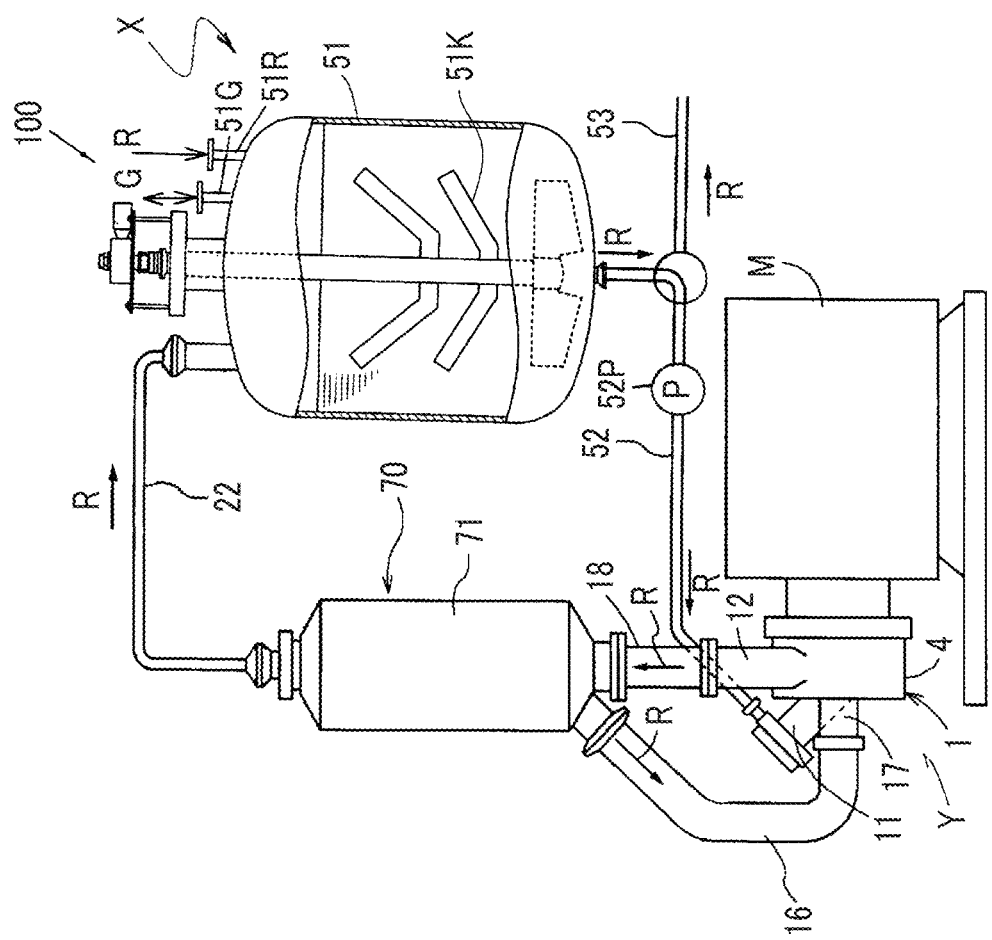

LIQUID SUBSTANCE STERILIZING METHOD AND APPARATUS

RELATED APPLICATIONS

Priority is claimed to Japanese Patent Application No. 2016-063092, filed Mar. 28, 2016, the entire content of which is incorporated herein by reference.

BACKGROUND

Technical Field

Certain Embodiments relates to liquid substance sterilization method and apparatus, and particularly, to liquid substance sterilizing method and apparatus that performs sterilization of a liquid substance by causing cavitation in the liquid substance and thereby generating plasma with a plasma generation mechanism in air bubbles generated in the liquid substance by the cavitation.

Description of Related Art

In order to perform sterilization of a liquid substance, the relates art discloses a method of causing cavitation in the liquid substance, and crushing and sterilizing microorganisms in the liquid substance due to impulse waves generated at the time of collapse of air bubbles generated by this cavitation.

Additionally, the related art also discloses a method of causing cavitation in the liquid substance, creating active oxygen, such as a hydroxyl radical, in the liquid substance by generating plasma in air bubbles generated by this cavitation, and sterilizing microorganisms in the liquid substance due to an oxidization force of the active oxygen in addition to impulse waves generated at the time of collapse of the air bubbles generated by the cavitation.

SUMMARY

According to a first embodiment of the present invention, there is provided a liquid substance sterilization method for performing a sterilizing a liquid substance by causing cavitation in the liquid substance and generating plasma with a plasma generation mechanism in air bubbles generated in the liquid substance by the cavitation. The method includes causing the cavitation in the liquid substance by stirring the liquid substance with a rotary blade.

Additionally, according to a second embodiment of the present invention, there is provided a liquid substance sterilization method for performing sterilizing a liquid substance by causing cavitation in the liquid substance and generating plasma with a plasma generation mechanism in air bubbles generated in the liquid substance by the cavitation. The method includes causing the cavitation in the liquid substance behind an obstacle by installing the obstacle in a flow passage for the liquid substance to which a flow speed is imparted.

Additionally, according to a third embodiment of the present invention, a liquid substance sterilizing apparatus of the invention for carrying out the liquid substance sterilization method of the above first embodiment includes a suction stirring pump that suctions a liquid substance under a negative pressure with a negative-pressure suction force generated by rotation of a rotary blade and causes cavitation by stirring the liquid substance subjected to the suction under the negative pressure with the rotary blade; and a plasma generation mechanism that generates plasma in air bubbles generated in the liquid substance by the cavitation.

Additionally, according to a fourth embodiment of the present invention, a liquid substance sterilizing apparatus of the invention for carrying out the liquid substance sterilization method of the above second embodiment includes a flow speed imparting mechanism that imparts a flow speed to a liquid substance; an obstacle that is installed in a flow passage for the liquid substance to which the flow speed is imparted by the flow speed imparting mechanism, thereby causing cavitation in the liquid substance to which the flow speed is imparted; and a plasma generation mechanism that generates the plasma in air bubbles generated in the liquid substance by the cavitation.

BRIEF DESCRIPTION OF THE DRAWINGS

FIGS. 1A and 1B illustrate an embodiment of a liquid substance sterilizing apparatus of the invention, FIG. 1A is a schematic configuration diagram and, FIG. 1B is an explanatory view of a plasma generation mechanism.

FIG. 7A is a longitudinal sectional view, and FIG. 7B is a cross-sectional view as seen from a downstream side.

DETAILED DESCRIPTION

Figure 2:
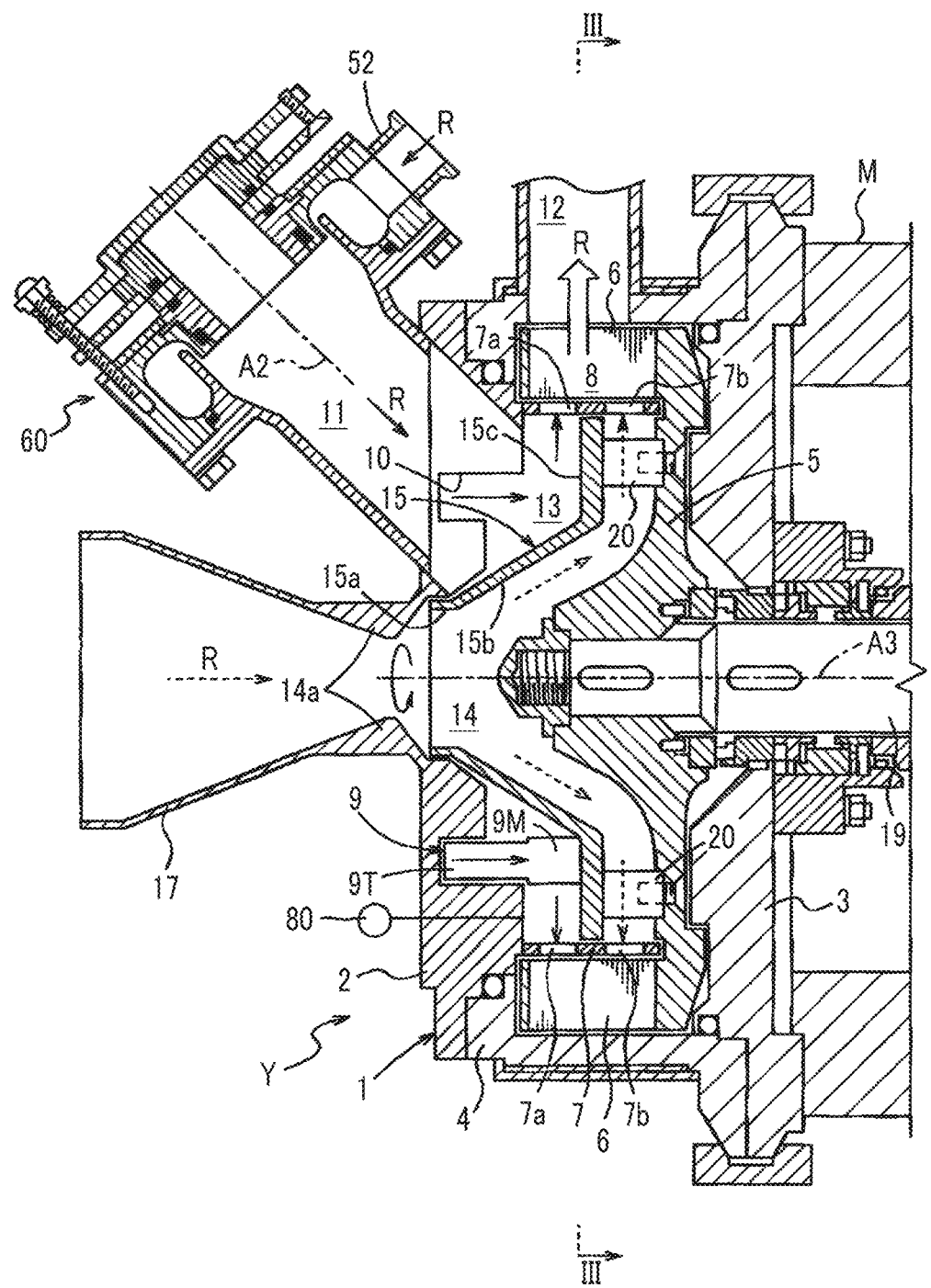
FIG. 2 is an explanatory view illustrating an internal structure of a suction stirring pump.

Meanwhile, since the liquid substance sterilization method described in the related art out of the above liquid substance sterilization methods crushes and sterilizes the microorganisms in the liquid substance due to the impulse waves generated at the time of the collapse of the air bubbles generated by the cavitation, there are problems that sterilizing power is small and a sterilizing effect cannot be easily obtained (see the results of the sterilization test to be described below).

Additionally, since the liquid substance sterilization method described in the related art sterilizes the microorganisms in the liquid substance due to the oxidization force of the active oxygen in addition to the impulse waves generated at the time of the collapse of the air bubbles generated by the cavitation, there is a problem that large sterilizing power is obtained, whereas a facility or apparatus is enlarged, such as providing a storage tank that stores the liquid substance.

It is desirable to provide liquid substance sterilization method and apparatus that can obtain a great sterilizing effect with a small-sized facility or apparatus, in view of the problems that the above liquid substance sterilization method has.

In this case, the cavitation may be caused in the liquid substance by passing the liquid substance, to which a flow speed is imparted by performing stirring with the rotary blade, through a throttle flow passage.

In this case, the suction stirring pump may be configured to include a throttle flow passage that allows the liquid substance, to which a flow speed is imparted by performing stirring with the rotary blade, to pass therethrough.

Additionally, a configuration in which a plasma generation mechanism is provided in a discharge pipe that is connected to the suction stirring pump and allows the liquid substance to be discharged therethrough may be adopted.

Additionally, a configuration in which a circulation flow passage that allows the liquid substance discharged from the suction stirring pump to be circulated to the suction stirring pump is provided may be adopted.

Additionally, the obstacle may be constituted by an electrode of the plasma generation mechanism or may be constituted by an obstacle installed on an upstream side of the electrode of the plasma generation mechanism.

According to the liquid substance sterilization methods and the liquid substance sterilization apparatus, the cavitation can be caused in the liquid substance by stirring the liquid substance with the rotary blade, the plasma can be generated with the plasma generation mechanism in the air bubbles generated in the liquid substance by the cavitation, and the microorganisms in the liquid substance can be sterilized due to the oxidization force of the oxygen radical created by the generation of the plasma. Particularly, by stirring the liquid substance with the rotary blade, fine air bubbles caused by the cavitation can be efficiently generated in the liquid substance, the plasma can be efficiently and uniformly generated by the plasma generation mechanism in these fine air bubbles, and a great sterilizing effect can be obtained with a small-sized facility or apparatus.

Additionally, the fine air bubbles caused by the cavitation can be efficiently generated in the liquid substance bypassing the liquid substance, to which the flow speed is imparted by performing stirring with the rotary blade, through the throttle flow passage.

Additionally, by providing the plasma generation mechanism in the discharge pipe that is connected to the suction stirring pump and allows the liquid substance to be discharged therethrough, the plasma can be efficiently and uniformly generated by the plasma generation mechanism in the air bubbles generated in the liquid substance by the cavitation.

Additionally, by including the circulation flow passage that allows the liquid substance discharged from the suction stirring pump to be circulated to the suction stirring pump, thereby circulating the liquid substance discharged from the suction stirring pump to the suction stirring pump, the treatment time of the liquid substance can be set arbitrarily, and an efficient reliable sterilizing effect can be obtained.

Additionally, according to the liquid substance sterilization methods and the liquid substance sterilization apparatus, the cavitation can be caused in the liquid substance by installing the obstacle in the flow passage for the liquid substance to which the flow speed is imparted, the plasma can be generated with the plasma generation mechanism in the air bubbles generated in the liquid substance by the cavitation, and the microorganisms in the liquid substance can be sterilized due to the oxidization force of the oxygen radical created by the generation of the plasma. Particularly, by installing the obstacle in the flow passage of the liquid substance to which the flow speed is imparted, the fine air bubbles caused by the cavitation can be efficiently generated in the liquid substance, the plasma can be efficiently and uniformly generated by the plasma generation mechanism in these fine air bubbles, and a great sterilizing effect can be obtained with a small-sized facility or apparatus.

Additionally, the fine air bubbles caused by the cavitation can be efficiently generated in the liquid substance by a simple mechanism by constituting the obstacle with the electrode of the plasma generation mechanism or constituting the obstacle with the obstacle installed on the upstream side of the electrode of the plasma generation mechanism.

Hereinafter, embodiments of liquid substance sterilization method and apparatus of the invention will be described.

Outline of Liquid Substance Sterilization Method

A liquid substance sterilization method of the invention causes cavitation in a liquid substance by stirring the liquid substance with a rotary blade, generates plasma with a plasma generation mechanism in air bubbles generated in the liquid substance by the cavitation, and sterilizes microorganisms in the liquid substance due to an oxidization force of an oxygen radical created by the generation of the plasma.

Accordingly, the fine air bubbles caused by the cavitation can be efficiently generated in the liquid substance, the plasma can be efficiently and uniformly generated by the plasma generation mechanism in these fine air bubbles, and a great sterilizing effect can be obtained with a small-sized facility or apparatus.

Liquid Substance Sterilizing Apparatus

Hereinafter, an embodiment of a liquid substance sterilizing apparatus of the invention in which the liquid substance sterilization method of the invention is embodied will be described with reference to FIGS. 1 to 6.

The outline of the liquid substance sterilizing apparatus 100 is illustrated in FIG. 1.

The sterilizing apparatus 100 is configured to include a liquid substance supply part X to that supplies a liquid substance R, a suction stirring pump Y that suctions the liquid substance R supplied from the liquid substance supply part X under negative pressure to stir the suctioned liquid substance, a plasma generation mechanism Z that generates plasma in air bubbles generated in the liquid substance R discharged from the suction stirring pump Y by cavitation, and a recirculation mechanism unit 70 that circulates and supplies at least a portion of the liquid substance R discharged from the suction stirring pump Y to the suction stirring pump Y, on a downstream side of the plasma generation mechanism.

Liquid Substance Supply Part

As illustrated in FIGS. 1A and 1B, the liquid substance supply part X is configured such that the liquid substance R stored in a storage tank 51 is continuously supplied to a first supply part 11 of the suction stirring pump Y.

Specifically, the liquid substance supply part X is configured to include the storage tank 51 that stores the liquid substance R to be supplied via a liquid substance supply pipe 51R and delivers the stored liquid substance, a supply pipe 52 that has a delivery pump 52P for delivering the liquid substance R from the storage tank 51 interposed therein, a flow rate adjusting valve (not illustrated) that adjusts the flow rate of the liquid substance R to be delivered from the storage tank 51 to the supply pipe 52 at a setting flow rate, and an introduction mechanism 60 that connects the supply pipe 52 to the first supply part 11 of the suction stirring pump Y.

Here, as will be described below, the storage tank 51 is configured such that the liquid substance R from a discharge passage 22 is introduced thereinto.

Additionally, a stirring mechanism 51K is disposed in the storage tank 51, and an inlet/outlet pipe 51G for air (gas) G that maintains the inside of the storage tank 51 at the atmospheric pressure, and a discharge passage 53 for the liquid substance R subjected to sterilization treatment are connected to the storage tank.

Suction Stirring Pump

The suction stirring pump Y will be described with reference to of FIGS. 1 and 2 to 6.

As illustrated in FIG. 2, the suction stirring pump Y is configured to include a casing 1 including a cylindrical outer peripheral wall part 4 of which both end openings are closed by a front wall part 2 and a rear wall part 3, and include a rotor 5 that is concentrically provided in a rotationally drivable manner inside the casing 1, a cylindrical stator 7 that is concentrically disposed inside the casing 1 and fixed to the front wall part 2, and a pump drive motor M that rotationally drives the rotor 5.

Figure 3:
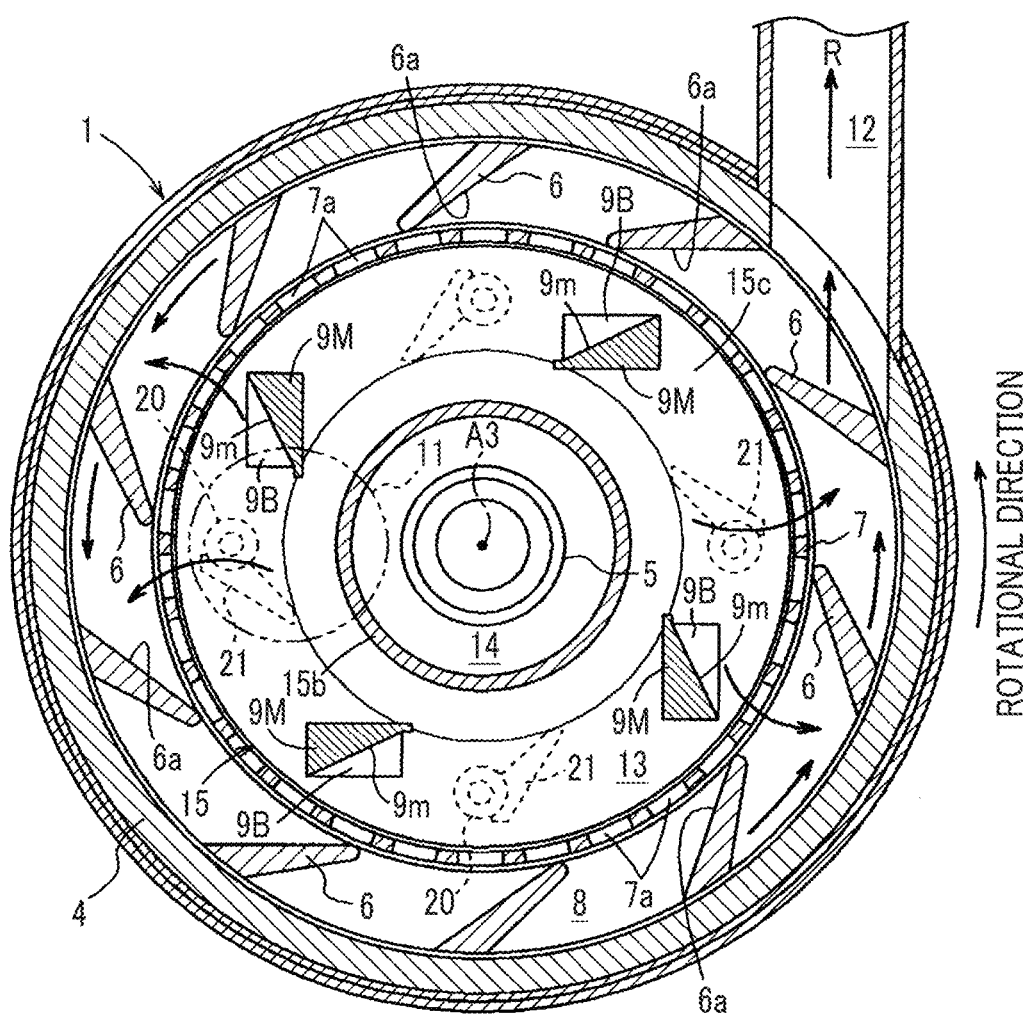
FIG. 3 is a sectional view as seen in a direction of FIG. 2.

As illustrated in FIG. 3, a plurality of rotary blades 6 are provided integrally with the rotor 5 on a radially outer side of the rotor 5 in a state where the rotary blades 6 protrude to a front side (left side of FIG. 2) that is the front wall part 2 side, and are lined up at equal intervals in the circumferential direction.

A plurality of through-holes 7a and 7b serving as throttle flow passages are respectively provided to be lined up in the circumferential direction in the cylindrical stator 7, the stator 7 is located on the front side (left side of FIG. 2) of the rotor 5 and on radial inner sides of the rotary blades 6, and is fixed to and disposed at the front wall part 2, and an annular blade chamber 8 which serves as a discharge chamber and which the rotary blades 6 go around is formed between the stator 7 and the outer peripheral wall part 4 of the casing 1.

Figure 4:
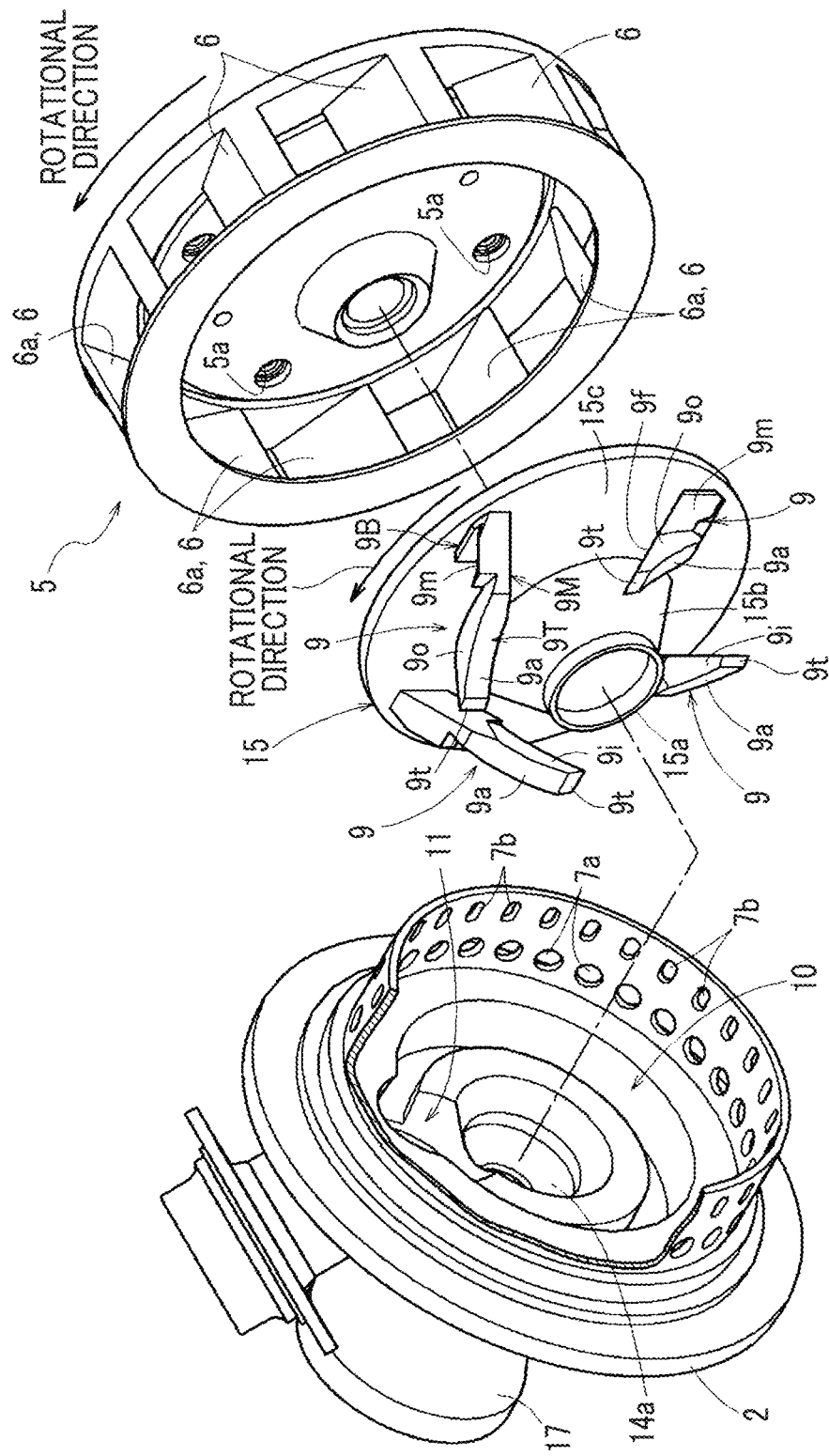
FIG. 4 is an exploded perspective view illustrating an internal structure of a suction stirring pump.

As illustrated in FIGS. 2 to 4, the first supply part 11, which suctions and introduces the liquid substance R into the inside of the casing 1 through the rotation of the rotary blades 6 via the introduction mechanism 60, is provided at a position further shifted to an outer peripheral side than a central axis (an axial center A3 of the casing 1) of the front wall part 2.

As illustrated in FIGS. 2 and 4, an annular groove 10 is formed in an inner surface of the front wall part 2 of the casing 1, and the first supply part 11 is provided in a state where the first supply part communicates with the annular groove 10.

As illustrated in FIGS. 2 and 3, a cylindrical discharge part 12 that discharges the liquid substance R is provided in one place in the circumferential direction of the cylindrical outer peripheral wall part 4 of the casing 1 in a state where the discharge part extends in a tangential direction of the outer peripheral wall part 4 and communicates with the blade chamber 8.

As illustrated in FIGS. 1A and 1B and FIGS. 2 and 6, in this embodiment, the liquid substance R discharged from the discharge part 12 is supplied to a recirculation mechanism unit 70 through a discharge passage 18, a second supply part 17 that circulates and supplies the liquid substance R, from which the air bubbles have been separated in a cylindrical container 71 serving as a separation part of the recirculation mechanism unit 70, via a circulation flow passage 16 into the casing 1, is provided at a central part (concentric with the axial center A3) of the front wall part 2 of the casing 1.

Additionally, as illustrated in FIGS. 2 to 4, a partition plate 15, which partitions an inner peripheral side of the stator 7 into a first introduction chamber 13 on the front wall part 2 side and a second introduction chamber 14 on the rotor 5 side, is provided on the front side of the rotor 5 in a state where the partition plate rotates integrally with the rotor 5, and a scrape-out blade 9 is provided on the front wall part 2 side of the partition plate 15.

A plurality of (four in FIG. 4) the scrape-out blades 9 are concentrically provided at equal intervals in the circumferential direction, and each scrape-out blade 9 is disposed so as to go around integrally with the rotor 5 in a state where a tip part 9T has entered the annular groove 10.

The first introduction chamber 13 and the second introduction chamber 14 are configured so as to communicate with the blade chamber 8 via the plurality of through-holes 7a and 7b of the stator 7, the first supply part 11 is configured so as to communicate with the first introduction chamber 13, and the second supply part 17 is configured so as to communicate with the second introduction chamber 14.

Specifically, the first introduction chamber 13 and the blade chamber 8 communicate with the plurality of through-holes 7a on the first introduction chamber 13 that are disposed at equal intervals in the circumferential direction in a portion that faces the first introduction chamber 13 in a stator 7, and the second introduction chamber 14 and the blade chamber 8 communicate with the plurality of through-holes 7b on the second introduction chamber 14 side that are disposed at equal intervals in the circumferential direction in a portion that faces the second introduction chamber 14 in the stator 7.

Respective parts of the suction stirring pump Y will be described.

As illustrated in FIG. 2, the rotor 5 is configured in a shape that a front surface thereof swells in a substantially truncated conical shape, and the plurality of rotary blades 6 are provided on an outer peripheral side of the rotor so to be lined up at equal intervals in a state where the rotary blades protrude forward.

In addition, in FIG. 3, ten rotary blades 6 are disposed at equal intervals in the circumferential direction.

Additionally, each rotary blade 6 is formed to protrude from the outer peripheral side of the rotor 5 to the inner peripheral side thereof so as to be inclined backward in a rotational direction as they move toward the outer peripheral side from the inner peripheral side, and the internal diameter of a tip part of the rotary blade 6 is formed with a slightly larger diameter than the external diameter of the stator 7.

The rotor 5 is coupled to a drive shaft 19 of the pump drive motor M inserted into the casing 1 through the rear wall part 3 in a state where the rotor is located concentrically with the casing 1 within the casing 1, and is rotationally driven by the pump drive motor M.

The rotor 5 is configured such that the rotor is rotationally driven in a direction in which the tip part of the rotary blade 6 is located on the front side as seen in an axial center direction (as seen in a direction III-III of FIG. 2 as illustrated in FIG. 3), and thereby, cavitation (local boiling) occurs in a surfaces (back surface) 6a located on the backward side in the rotational direction of the rotary blade 6.

As illustrated in FIGS. 2 and 4 and FIGS. 5A to 5C, the partition plate 15 is configured in a substantial funnel shape having a slightly small external diameter than the internal diameter of the stator 7.

The funnel-shaped partition plate 15 is configured, specifically, in a shape including a funnel-shaped part 15b, which opens to a tubular sliding part 15a of which a top part protrudes in a tubular shape, at a central part thereof and including an annular flat plate part 15c, which is orthogonal to the axial center A3 of the casing 1 together with a front surface and a rear surface, at an outer peripheral part of the funnel-shaped part 15b thereof.

As illustrated in FIGS. 2 and 3, the partition plate 15 is attached to an attachment part 5a of a front surface of the rotor 5 via interval-maintaining members 20 disposed in a plurality of (four places in this embodiment) at regular intervals in the circumferential direction in a posture where the tubular sliding part 15a at the top part thereof faces the front wall part 2 side of the casing 1.

Figure 5A:
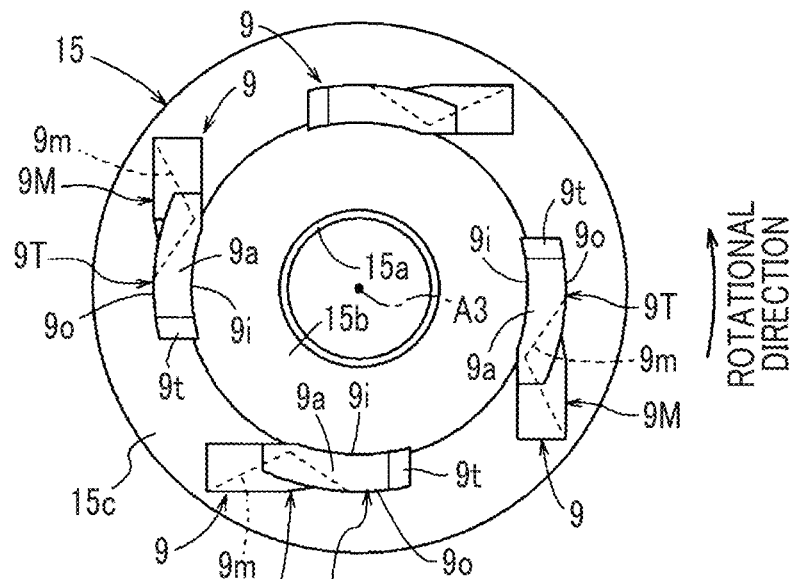
FIGS. 5A-5C are schematic configuration diagrams of a partition plate.
Figure 5B:
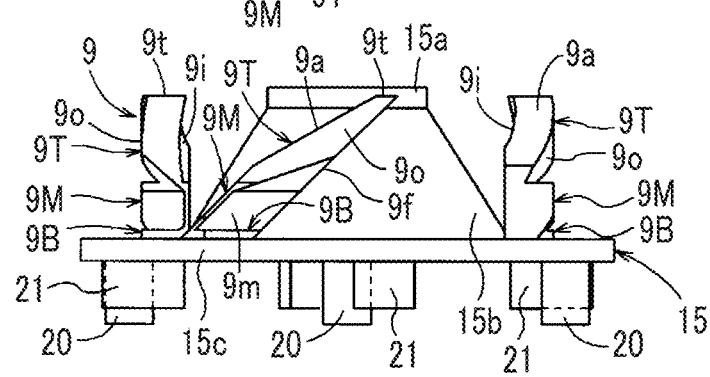
Figure 5C:
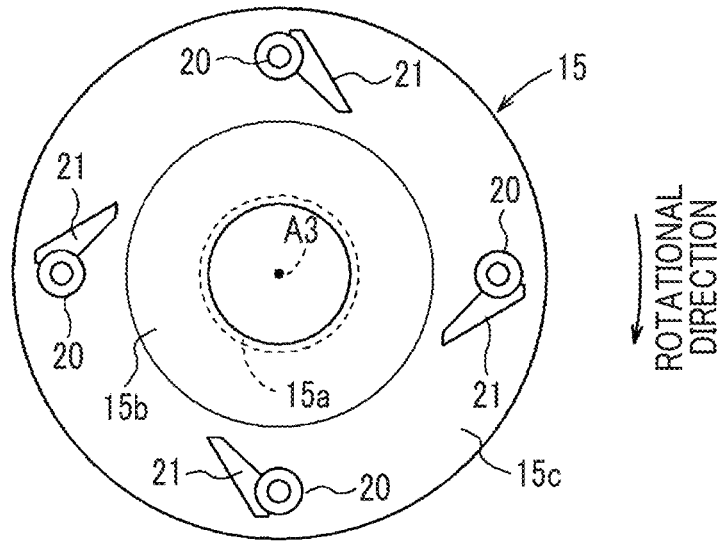

As illustrated in FIGS. 3 and 5C, when the partition plate 15 is attached to the rotor 5 via the interval-maintaining members 20 in the plurality of respective places, stirring blades 21 are integrally assembled to the partition plate 15 in a posture where the stirring blades face the rear wall part 3 side of the casing 1, and if the rotor 5 is rotationally driven, four stirring blades 21 are configured so as to rotate integrally with the rotor 5.

As illustrated in FIGS. 2 and 4, in this embodiment, the cylindrical second supply part 17 is provided at the central part of the front wall part 2 of the casing 1 concentrically with the casing 1.

A throttle part 14a, having a slightly smaller diameter from the internal diameter of the circulation flow passage 16 and having a smaller diameter than and consequently having a smaller flow passage area than the tubular sliding part 15a of the partition plate 15, is formed in the second supply part 17.

When the rotary blades 6 of the rotor 5 rotate, the liquid substance R is discharged via the discharge part 12 and the liquid substance R is introduced via the throttle part 14a of the second supply part 17. Thus, the inside of the suction stirring pump Y is decompressed.

As illustrated in FIGS. 2 to 4, the first supply part 11 is provided in the front wall part 2 so as to be located in a lateral side of the opening part of the second supply part 17 with respect to the inside of the casing 1, in a state where an opening part (inlet part) opening to the inside of the casing 1 includes a portion of the annular groove 10 in the circumferential direction therein.

Additionally, the first supply part 11 is provided in the front wall part 2 of the casing 1 in a downwardly-inclined posture where an axial center A2 becomes parallel to the axial center A3 of the casing 1, in a plan view (as seen in an upward-and-downward direction of FIGS. 1 and 2), and the axial center A1 approaches the axial center A3 of the casing 1 as the axial center A2 approaches the front wall part 2 of the casing 1, in a view (as seen in front-and-back direction of a paper plane of FIGS. 1 and 2) as seen in a horizontal direction orthogonal to the axial center A3 of the casing 1.

Incidentally, a downwardly-inclined angle of the first supply part 11 with respect to the horizontal direction (leftward-rightward direction of FIGS. 1A and 1B and FIG. 2) is about 45 degrees.

As illustrated in FIGS. 2 and 4, the stator 7 is attached to an inner surface (a surface that faces the rotor 5) of the front wall part 2 of the casing 1, and is fixed such that the front wall part 2 of the casing 1 and the stator 7 become integral with each other.

In the stator 7, the plurality of through-holes 7a on the first introduction chamber 13 side disposed in the portion that faces the first introduction chamber 13 are formed in a substantially circular shape, and the total flow passage area of the plurality through-holes 7a on the first introduction chamber 13 side is set so as to become smaller than the flow passage area of the first introduction chamber 13. Additionally, the plurality of through-holes 7b on the second introduction chamber 14 side disposed in the portion that faces the second introduction chamber 14 are formed in a substantially elliptical shape, and the total flow passage area of the plurality of through-holes 7b on the second introduction chamber 14 side is set so as to become smaller than the flow passage area of the second introduction chamber 14.

When the rotary blades 6 of the rotor 5 rotate, the liquid substance R is discharged via the discharge part 12, the liquid substance R is supplied via the through-holes 7a on the first introduction chamber 13, and the liquid substance R is introduced via the second supply part 17. Thus, the inside of the suction stirring pump Y is decompressed.

As illustrated in FIG. 4 and FIGS. 5A to 5C, in this embodiment, each scrape-out blade 9 is formed in a rod shape, and is fixed such that base end part 9B of the rod-shaped scrape-out blade 9 is fixed to so as to rotate integrally with the rotor 5, in an inclined posture where the scrape-out blade is located closer to the front wall part 2 side as becoming closer to tip sides of the rod-shaped scrape-out blade 9, as seen in a radial direction (as seen in the front-and-back direction of the paper plane of FIG. 5B) of the rotor 5, and is located closer to the radial inner side of the rotor 5 as becoming closer to a tip side of the rod-shaped scrape-out blade 9, as seen in the axial center direction (as seen in the front-and-back direction of the paper plane of FIG. 5A) of the rotor 5, and the rotor 5 is rotationally driven in a direction (a direction orientation illustrated by an arrow in FIG. 2 to FIGS. 5A to 5C) in which a tip of the scrape-out blade 9 is located on the front side as seen in the axial center direction (as seen in the front-and-back direction of the paper plane of FIG. 5A).

The scrape-out blades 9 will be described on the basis of FIG. 3 to FIGS. 5A to 5C.

Each scrape-out blade 9 is configured in a rod shape including the base end part 9B fixed to the partition plate 15, an intermediate part 9M exposed to the first introduction chamber 13, and the tip part 9T that is fitted into (that is, enters) the annular groove 10 in series from a base end toward a tip.

As illustrated in FIGS. 3, 4, and 5B, the base end part 9B of the scrape-out blade 9 is configured in a substantially rectangular plate shape.

As illustrated in FIG. 3, FIG. 4, FIGS. 5A, and 5B, the intermediate part 9M of the scrape-out blade 9 is configured in a substantially triangular columnar shape of which a cross-sectional shape becomes a substantially triangular shape (particularly refer to FIG. 3).

By providing the scrape-out blade 9 in the inclined posture as described above, one side surface 9m (hereinafter referred to as a "diffusion surface") that faces a forward side in the rotational direction of the rotor 5 among three side surfaces of the triangular columnar intermediate part 9M is configured to face the radial outer side (hereinafter may be referred to as "obliquely outward direction") with respect to the radial direction of the rotor 5 in a forwardly lowered manner such that the one side surface is inclined to the forward side in the rotational direction of the rotor 5 (particularly refer to FIG. 4 and FIGS. 5A to 5C).

That is, by providing the rod-shaped scrape-out blade 9 in the inclined posture as described above, the intermediate part 9M exposed to the first introduction chamber 13 in the scrape-out blade 9 is located closer to the radial outer side of the rotor 5 than the tip part 9T fitted into the annular groove 10, and the diffusion surface 9m that faces the forward side in the rotational direction of the intermediate part 9M is inclined in the oblique outward direction with respect to the radial direction of the rotor 5 in a forwardly lowered manner such that the diffusion surface is inclined toward the forward side in the rotational direction of the rotor 5.

Accordingly, the liquid substance R scraped out from the annular groove 10 by the tip part 9T of the scrape-out blade 9 is guided so as to flow toward the radial outer side of the rotor 5 within the first introduction chamber 13 by the diffusion surface 9m of the intermediate part 9M of the scrape-out blade 9.

As illustrated in FIG. 4, FIG. 5A, and FIG. 5B, the tip part 9T of the scrape-out blade 9 has a substantially square columnar shape of which the cross-sectional shape becomes a substantially rectangular shape, and is configured in a circular-arc shape in which, as seen in the axial center direction (as seen in the front-and-back directional of the paper plane of FIG. 5A) of the rotor 5, an outward side surface 9o that faces the radial outer side of the rotor 5 among the four side surfaces runs along an inward inner surface that faces the radial inner side in the inner surface of the annular groove 10, and an inward side surface 9i that faces the radial inner side of the rotor 5 among the four side surfaces runs along an outward inner surface that faces the radial outer side in the inner surface of the annular groove 10.

Additionally, a rake-out surface 9f that faces the forward side in the rotational direction of the rotor 5 among the four side surfaces of the square columnar tip part 9T is configured so as to face the radial outer side (hereinafter may be referred to as an "obliquely outward direction") with respect to the radial direction of the rotor 5 in a forwardly lowered manner such that the rake-out surface is inclined toward the forward side in the rotational direction of the rotor 5.

Accordingly, the liquid substance R scraped out from the annular groove 10 by the tip part 9T of the scrape-out blade 9 is released into the first introduction chamber 13 toward the radial outer side of the rotor 5 by the scrape-out surface 9f of the tip part 9T of the scrape-out blade 9.

Moreover, a tip surface 9t of the tip part 9T of the scrape-out blade 9 is configured so as to become parallel to a bottom surface of the annular groove 10 in a state where the tip part 9T is fitted into the annular groove 10.

Additionally, if the rotor 5 is rotationally driven in the direction in which the tip part of the rotary blade 9 is located on the front side as seen in the axial center direction (as seen in the front-and-back directional of the paper plane of FIG. 5A), a surface (back surface) 9a located on the backward side in the rotational direction is formed in each of the base end part 9B, the intermediate part 9M, and the tip part 9T of the scrape-out blade 9.

The scrape-out blade 9 is configured such that the cavitation (local boiling) occurs in the back surface 9a when the scrape-out blade 9 rotates.

The four scrape-out blades 9 configured in the shape as described above are provided by fixing the base end parts 9B thereof to the annular flat plate part 15c of the partition plate 15, in a form in which the blades are lined up in the circumferential direction at intervals of 90°, in the inclined posture as described above.

As illustrated in FIG. 2, the partition plate 15 provided with the scrape-out blades 9 is attached to the attachment part 5a of the front surface of the rotor 5 in a state where the partition plate is spaced apart from the front surface of the rotor 5 by the interval-maintaining members 20, and the rotor 5 is disposed within the casing 1 in a state where the tubular sliding part 15a of the partition plate 15 is slidably and rotatably fitted into the second supply part 17.

Accordingly, the tapered second introduction chamber 14 having a smaller diameter as it becomes closer to the front wall part 2 side of the casing 1 is formed between the swelled front surface of the rotor 5, the rear surface of the partition plate 15, and the second supply part 17 is configured so as to communicate with the second introduction chamber 14 via the tubular sliding part 15a of the partition plate 15.

Additionally, the annular first introduction chamber 13 that communicates with the first supply part 11 is formed between the front wall part 2 of the casing 1 and the front surface of the partition plate 15.

If the rotor 5 is rotationally driven, the partition plate 15 rotates integrally with the rotor 5 in a state where the tubular sliding part 15a slides on the second supply part 17. As a result, the second supply part 17 is configured so as to maintain a state where the second supply part communicates with the second introduction chamber 14 via the sliding part 15a of the partition plate 15, even in a state where the rotor 5 and the partition plate 15 rotate.

Recirculation Mechanism Unit

The recirculation mechanism unit (an example of the separation part) 70 is configured so as to separate the liquid substance R within the cylindrical container 71, and as illustrated in FIG. 1, is configured so as to separate air bubbles from the liquid substance R supplied through the discharge passage 18 from the discharge part 12 of the suction stirring pump Y and to separate and supply some (for example, an arbitrary proportion of 10% to 90%) of the liquid substance R to the circulation flow passage 16 and the remaining liquid substance R to the discharge passage 22 together with the air bubbles included in the liquid substance R, respectively.

The discharge passage 18 and the circulation flow passage 16 are respectively connected to a lower part of the cylindrical container 71, and the discharge passage 22 is connected to the storage tank 51 from a discharge part 73 formed at an upper part of the cylindrical container 71.

Figure 6:
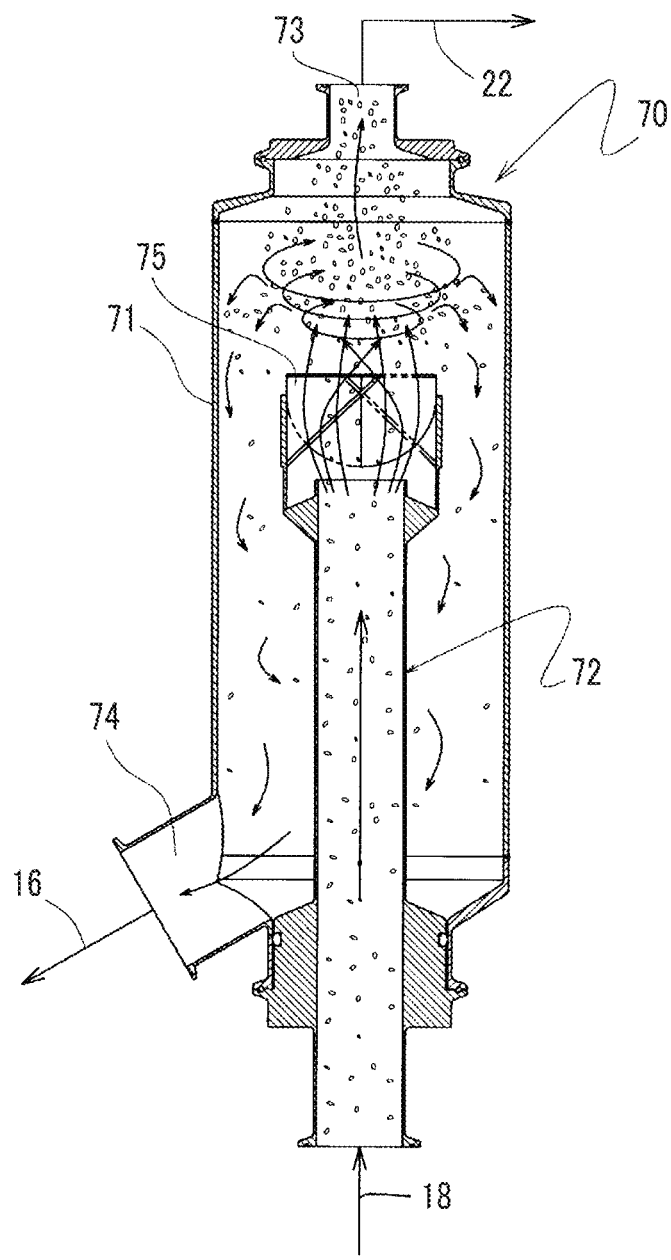
FIG. 6 is an explanatory view illustrating an internal structure of a separation part of a recirculation mechanism unit.

Here, as illustrated in FIG. 6, the recirculation mechanism unit 70 is disposed such that an introduction pipe 72 having the discharge passage 18 connected thereto protrudes thereinto from a bottom surface of the cylindrical container 71, includes the discharge part 73 connected to the discharge passage 22 at an upper part of the cylindrical container 71, includes a circulation part 74 connected to the circulation flow passage 16 at a lower part of the cylindrical container 71, and is configured such that a twist plate 75 that swirls a flow of the liquid substance R discharged from the introduction pipe 72 is disposed at a discharge upper end of the introduction pipe 72.

Accordingly, the liquid substance R that does not include air bubbles is supplied into the second introduction chamber 14 via the circulation flow passage 16.

Control Unit

Although not illustrated, the control unit provided in the sterilizing apparatus 100 consists of a well-known arithmetic processing unit including a CPU, a storage unit, and the like, and is configured to be capable of control the operation of respective apparatuses, such as the liquid substance supply part X and the suction stirring pump Y that constitute the sterilizing apparatus 100.

Particularly, the control unit is configured to be capable of controlling the circumferential speed (the rotational speed of the rotor 5) of each rotary blade 6, and is configured to be capable of setting the circumferential speed (the rotational speed of the rotor 5) of the rotary blade 6 such that the pressures within the first introduction chamber 13 and the second introduction chamber 14 are brought into predetermined negative pressure states and rotating the rotary blade 6 at the set circumferential speed (the rotational speed of the rotor 5), thereby forming at least a region within the blade chamber 8 immediately after passing through the through-holes 7a on the first introduction chambers 13 of the stator 7 and the through-holes 7b on the second introduction chamber 14 side as a fine-air-bubble region (air bubble generation region caused by the cavitation (local boiling)) where many fine air bubbles (micro bubbles) of the liquid substance R have been generated, continuously over the entire circumference within the blade chamber 8.

Here, a pressure gauge 80 for measuring the pressures within the first introduction chamber 13 and the second introduction chamber 14 (here, the pressure within the first introduction chamber 13 (here, the first introduction chamber 13 and the first second introduction chamber 14 have an approximately equal pressure) in the present embodiment) is provided.

Plasma Generation Mechanism in Liquid

The plasma generation mechanism Z is disposed in the discharge passage 18 which is connected to the discharge part 12 of the suction stirring pump Y and through which the liquid substance R passes.

The plasma generation mechanism Z, as illustrated in FIG. 1B, is constituted by electrodes 81 that are installed within the discharge passage 18 that connects the discharge part 12 and the recirculation mechanism unit 70 of the suction stirring pump Y together and are made of metals, such as copper and tungsten, and a power source 82 for applying a pulse voltage to between the electrodes 81.

The plasma generation mechanism Z ionizes (plasmatizes) vaporized matter through high-voltage insulation breakdown discharge caused by the pulse voltage in an insulating air bubble region to generate plasma in a liquid.

In this case, it is preferable that a discharge form that occurs due to the pulse voltage, is glow discharge in which the electrodes 81 are installed to face a direction orthogonal to the discharge passage 18 though which the liquid substance R passes. Accordingly, it is possible to perform plasma treatment in liquid at a low temperature.

Active oxygen, such as a hydroxyl radical, can be generated in the liquid substance R through the plasma treatment in liquid, and microorganisms in the liquid substance R can be sterilized by an oxidization force of the active oxygen.

Additionally, a sterilizing effect caused by an electrical field between the electrodes 81 (an electrical field caused when a high voltage is applied to between the electrodes before the creation of the plasma) or ultraviolet rays released from the plasma at the time of the creation of the plasma can also be expected.

Operation of Sterilization Apparatus

Next, the operation of the sterilizing apparatus 100 will be described.

First, the liquid substance R that is a target for sterilization treatment is supplied to the storage tank 51 of the liquid substance supply part X via the liquid substance supply pipe 51R, and is stored in the storage tank.

Then, the rotor 5 is rotated while supplying the liquid substance R from the storage tank 51 of the liquid substance supply part X, and the operation of the suction stirring pump Y is continued for a predetermined time.

If the rotor 5 is rotationally driven and the partition plate 15 rotates integrally with the rotor 5, each scrape-out blade 9 that is concentrically provided in the partition plate 15 goes around in a state where the tip part 9T is fitted into the annular groove 10.

Accordingly, as illustrated by solid line arrows in FIGS. 2 and 3, the liquid substance R that has flowed through the first supply part 11 and has been introduced into the annular groove 10 is scraped out by the tip part 9T of the scrape-out blade 9 that is fitted into the annular groove 10 and goes around, and the scraped-out liquid substance R roughly flows through the inside of the first introduction chamber 13 in the rotational direction of the rotor 5 while running along the front surface of the funnel-shaped part 15b and the front surface of the annular flat plate part 15c in the partition plate 15. Further, the scraped-out liquid substance R passes through the through-holes 7a on the first introduction chamber 13 side of the stator 7 to flow into the blade chamber 8, flows through the inside of the blade chamber 8 in the rotational direction of the rotor 5, and is discharged from the discharge part 12.

The liquid substance R introduced into the annular groove 10 receives a shearing action when being scraped out by the tip part 9T of the scrape-out blade 9.

In this case, a shearing action is exerted between the outward side surface 90 of the tip part 9T of the scrape-out blade 9 and the inward inner surface of the inside annular groove 10, and between the inward side surface 9i of the tip part 9T of the scrape-out blade 9 and the outward inner surface of the inside annular groove 10.

Simultaneously, in the back surface 9a of the scrape-out blade 9 on the backward side in the rotational direction, the cavitation (local boiling) occurs when the scrape-out blade 9 rotates.

Additionally, a shearing action is exerted when the liquid substance passes through the through-holes 7a on the first introduction chamber 13 side of the stator 7.

That is, since a shearing force can be exerted on the liquid substance R within the first introduction chamber 13 and the local boiling can be caused, the scraped-out liquid substance R receives a shearing action from the scrape-out blade 9 and the through-holes 7a on the first introduction chamber 13 side, and the cavitation (local boiling) occurs in the back surface 9a of the scrape-out blade 9.

Meanwhile, the liquid substance R discharged from the discharge part 12 is supplied to the recirculation mechanism unit 70 through the discharge passage 18. In the recirculation mechanism unit 70, air bubbles are separated from the liquid substance R, some (for example, an arbitrary proportion of 10% to 90%) of the liquid substance R is supplied to the second supply part 17 of the suction stirring pump Y again via the circulation flow passage 16, and the remaining liquid substance R is supplied to the storage tank 51 via the discharge passage 22 together with the air bubbles included in the liquid substance R.

The liquid substance R supplied to the second supply part 17 of the suction stirring pump Y is introduced into the second introduction chamber 14 in a state where the flow rate thereof is limited via the throttle part 14a of the second supply part 17.

A shearing action is received by the plurality of stirring blades 21 that rotate within the second introduction chamber 14, and moreover, a shearing action is received also at the time of passage through the through-holes 7b on the second introduction chamber 14 side.

In this case, the liquid substance is introduced into the blade chamber 8 in a state where the flow rate thereof is limited via the through-holes 7b on the second introduction chamber 14 side.

Then, after each rotary blades 6 rotating at a high speed within the blade chamber 8 receive a shearing action, the liquid substance R is mixed with the liquid substance R from the first introduction chamber 13, and is discharged from the discharge part 12.

Here, the control unit is configured to be capable of controlling the circumferential speed (the rotational speed of the rotor 5) of each rotary blade 6, and is capable of setting the circumferential speed (the rotational speed of the rotor 5) of the rotary blade 6 such that the pressures within the first introduction chamber 13 and the second introduction chamber 14 are brought into predetermined negative pressure states and rotating the rotary blade 6 at the set circumferential speed (the rotational speed of the rotor 5), thereby forming at least a region within the blade chamber 8 immediately after passing through the through-holes 7a on the first introduction chambers 13 of the stator 7 and the through-holes 7b on the second introduction chamber 14 side as the fine-air-bubble region (air bubble generation region caused by the cavitation (local boiling)) where many fine air bubbles (micro bubbles) of the liquid substance R have been generated, continuously over the entire circumference within the blade chamber 8.

In this case, when the suction stirring pump Y is being operated, the pressures within the first introduction chamber 13 and the second introduction chamber 14 are set to bring about the negative pressure state of a range of −0.01 to 0.10 MPa, preferably −0.03 to −0.09 MPa, and more preferably 0.04 to −0.08 MPa, and the circumferential speed of the rotary blade 6 of the suction stirring pump Y is set to 6 to 80 m/s, preferably, 15 to 50 m/s.

Here, the negative pressure state means the pressures within the first introduction chamber 13 and the second introduction chamber 14 measured by the pressure gauge 80.

Meanwhile, in the sterilizing apparatus 100, the plasma generation mechanism Z is disposed in the discharge passage 18 which is connected to the discharge part 12 of the suction stirring pump Y and through which the liquid substance R is supplied and passes.

The pulse voltage is applied to between the electrodes 81 by the power source 82 of this plasma generation mechanism Z.

Accordingly, plasma is generated in air bubbles generated in the liquid substance R by the cavitation, and the plasma treatment in liquid is performed on the liquid substance R.

An oxygen radical, such as a hydroxyl radical, can be created in the liquid substance R through this plasma treatment in liquid, and microorganisms in the liquid substance R can be sterilized by an oxidization force of the oxygen radical created due to the generation of the plasma.

Additionally, the sterilizing effect caused by the electrical field between the electrodes 81 (the electrical field caused when a high voltage is applied to between the electrodes before the creation of the plasma or the ultraviolet rays released from the plasma at the time of the creation of the plasma) can also be expected.

Particularly, by stirring the liquid substance R with the rotary blade 6, the fine air bubbles caused by the cavitation can be efficiently generated in the liquid substance R, the plasma can be efficiently and uniformly generated by the plasma generation mechanism Z in these fine air bubbles, and a great sterilizing effect can be obtained with a small-sized facility or apparatus.

It is preferable that a discharge form that is caused due to the pulse voltage is glow discharge, and the plasma treatment in liquid at a low temperature can be performed, for example, the liquid substance can be treated at a normal temperature (Liquid temperature: 10° C. to 25° C.) by operating cooling means provided in the sterilizing apparatus 100, for example, jacket-cooling means (not illustrated) provided in the suction stirring pump Y.

Thus, the liquid substance R that is created and subjected to the sterilization treatment in this way is stored in the storage tank 51, and thereafter, the operation of the suction stirring pump Y is stopped.

Then, the liquid substance R that is stored in the storage tank 51 and subjected to the sterilization treatment is discharged via the discharge passage 53.

EXAMPLES

Next, a sterilization test performed using the sterilizing apparatus 100 is described.
Test Method
1. Test Bacteria
*Escherichia coli* NBRC 3301 (Colon *Bacillus*)
2. Culture medium for Measuring Number of Bacteria, and Culture Condition
SCDLP agar medium (made by NIHON PHARMACEUTICAL CO., LTD.), pour plate culture method, 35° C.±1° C., and two days
3. Preparation of Test Bacterial Suspension
After test bacteria were cultured for 18 to 24 hours at 35° C.±1° C., in a nutrient agar medium (made by EIKEN CHEMICAL CO., LTD.), the test bacteria were made to float in purified water, were prepared such that the number of bacteria reaches about $10^8$/mL, and were used as test bacterial suspension.
4. Pretreatment of Sample
In the sterilizing apparatus 100 (hereinafter referred to as a "sample"), a sodium hypochlorite solution prepared so as to reach about 0.02% was charged into the storage tank 51 of the liquid substance supply part X, and the sample was operated for 15 minutes on conditions without plasma. After draining, the inside of the sample was rinsed with tap water, 0.002% sodium thiosulfate-added tap water, and distilled water in this order, and draining was performed.
5. Test Operation
In the sample after the pretreatment, a test solution consisting of distilled water 1 L and test bacterial suspension 1 mL was charged into the storage tank 51 of the liquid substance supply part X. After the sample was operated on the test conditions shown below, the sample was stopped temporally and the test solution was taken. The sample was operated again after being taken. Additionally, the test solution after being taken was immediately diluted with the SCDLP agar medium (made by NIHON PHARMACEUTICAL CO., LTD.) by 100 times, and the number of viable bacteria in the test solution was measured using the culture medium for measuring the number of bacteria. In addition, the number of viable bacteria was also measured on the test solution before the operation of the sample, and was regarded as the number of viable bacteria at the time of start.
6. Test Condition
Rotational speed of pump-driving motor M that rotates rotor 5 of suction stirring pump Y of sterilizing apparatus 100: 7200 rpm
Plasma generation mechanism Z: 200 V (7A), 1.5 µs (pulse width), 60 kHz
Treatment time: 1, 5, 10, 20, and 30 minutes
Sample operating condition 1: tungsten electrode
Sample operating condition 2: copper electrode
Sample operating condition 3: with no plasma (only cavitation)
The results of the above sterilization test are shown in Table 1.

TABLE 1

| Operating Conditions | At Start | For 1 Minute | For 5 Minutes | For 10 Minutes | For 20 Minutes | For 30 Minutes |
|---|---|---|---|---|---|---|
| | | | Number of Viable Bacteria | | | |
| 1 | $6.2 \times 10^5$ | $3.0 \times 10^4$ | <100 | <100 | <100 | <100 |
| 2 | $7.9 \times 10^5$ | $2.1 \times 10^5$ | <100 | <100 | <100 | <100 |
| 3 | $7.1 \times 10^5$ | $7.9 \times 10^5$ | $7.7 \times 10^5$ | $6.6 \times 10^5$ | $6.4 \times 10^5$ | $5.0 \times 10^5$ |

As is also clear from the results of the sterilization test shown in Table 1, in the sample operating conditions 1 and 2 that the plasma treatment in liquid was used together for a cavitation action, it was confirmed that the treatment time for 5 minutes or more was taken, so that the number of viable bacteria could made to be substantially zero and a reliable sterilizing effect could be obtained.

Meanwhile, in the sample operating condition 3 in which there was only the cavitation action and the plasma treatment in liquid was not performed, it was confirmed that the sterilizing effect was small.

Meanwhile, in the above embodiment, the liquid substance R can be sterilized by adopting a configuration in which the cavitation (local boiling) occurs when the scrape-out blades 9 rotate or by forming the region within the blade chamber 8 immediately after passing through the through-holes 7a on the first introduction chamber 13 side of the stator 7 and the through-holes 7b on the second introduction chamber 14 side as the fine-air-bubble region (the air bubble generation region caused by the cavitation (local boiling)) where many fine air bubbles (micro bubbles) of the liquid substance R have been generated, thereby generating the plasma with the plasma generation mechanism in the air bubbles generated in the liquid substance R. However, the liquid substance can be sterilized by installing an obstacle in a flow passage of the liquid substance R to which a flow speed is imparted, in addition to these (or instead of these), thereby causing the cavitation (local boiling) in the liquid substance R behind this obstacle, thereby generating the plasma with the plasma generation mechanism Z in the air bubbles generated in the liquid substance R.

Figure 7A:
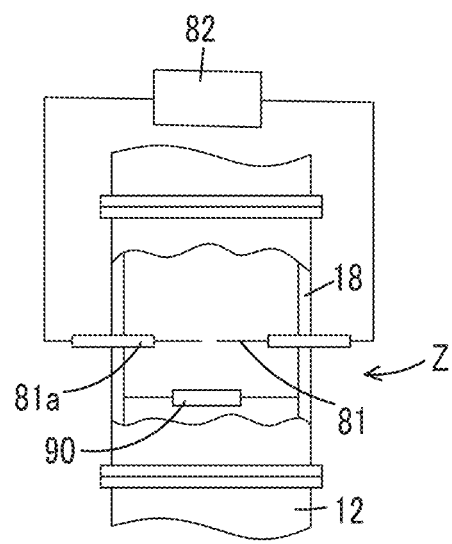
FIGS. 7A and 7B are explanatory views illustrating the embodiment of the liquid substance sterilizing apparatus of the invention and illustrating an obstacle and the plasma generation mechanism that cause cavitation in a liquid substance to which a flow speed is imparted.
Figure 7B:
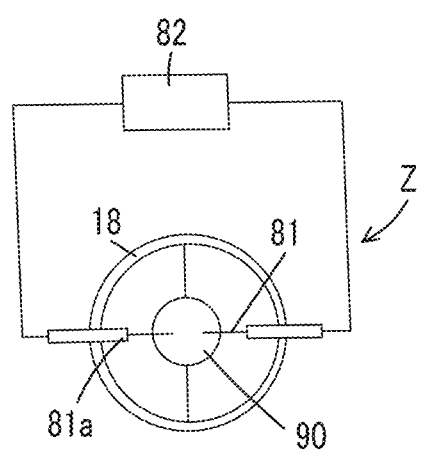

Specifically, as illustrated in FIG. 1B, the obstacle can be constituted by the electrodes 81 (including support members 81a of the electrodes 81) of the plasma generation mechanism Z installed in the discharge passage 18 which is a flow passage for the liquid substance R to which the flow speed is imparted and through which the liquid substance R passes, or as illustrated in FIG. 7, the obstacle can be constituted by an obstacle 90 (as the obstacle 90, in the present embodiment, a disk-shaped object is installed in the discharge passage 18 through which the liquid substance R passes. However, the shape of the obstacle 90 is not limited particularly. For example, objects with arbitrary shapes, such as a rod shape, can be installed) installed on an upstream side of the electrodes 81 of the plasma generation mechanism Z.

Accordingly, the fine air bubbles caused by the cavitation can be efficiently generated in the liquid substance R by a simple mechanism.

In this way, the plasma treatment in liquid can be performed by causing the cavitation the liquid substance R by installing the obstacle 90 or the electrodes 81 (including the support members 81a of the electrodes 81) of the plasma generation mechanism Z installed in the flow passage of the liquid substance to which the flow speed is imparted, and thereby generating the plasma with the plasma generation mechanism Z in the air bubbles generated in the liquid substance R.

An oxygen radical, such as a hydroxyl radical, can be created in the liquid substance R through this plasma treatment in liquid, and microorganisms in the liquid substance R can be sterilized by an oxidization force of the oxygen radical created due to the generation of the plasma.

In addition, in the present embodiment, the flow speed is imparted to the liquid substance R by the suction stirring pump Y. However, a flow speed imparting mechanism that imparts the flow speed to the liquid substance R is not limited to this, and a water flow generating mechanism for general-purpose pumps or the like can be used.

Although the liquid substance sterilization method and apparatus of the invention have been described above on the basis of the embodiment, the invention is not limited to the contents described in the above embodiment, and the configuration thereof can also be appropriately changed without departing from the scope thereof.

From the liquid substance sterilization method and apparatus of the invention, a great sterilizing effect can be obtained with a small-sized facility or apparatus. Therefore, in the invention, various kinds of liquid substance can be used as targets to be treated except that ballast water and a drain liquid that these types of liquid substance sterilization method and apparatus have adopted as the targets to be treated in the related art, and the invention can also be suitably used for applications of sterilization of industrial products (for example, food industrial products).

It should be understood that the invention is not limited to the above-described embodiment, but may be modified into various forms on the basis of the spirit of the invention. Additionally, the modifications are included in the scope of the invention.

What is claimed is:

1. A liquid substance sterilization method for sterilizing a liquid substance by causing cavitation in the liquid substance and generating plasma with a plasma generation mechanism in air bubbles generated in the liquid substance by the cavitation, the method comprising:
   causing the cavitation in the liquid substance by stirring the liquid substance with a rotary blade; and
   generating the plasma with the plasma generation mechanism.

2. The liquid substance sterilization method according to claim 1,
   wherein the cavitation is caused in the liquid substance by passing the liquid substance, to which a flow speed is imparted by performing stirring with the rotary blade, through a throttle flow passage.

3. A liquid substance sterilization method for sterilizing a liquid substance by causing cavitation in the liquid substance and generating plasma with a plasma generation mechanism in air bubbles generated in the liquid substance by the cavitation, the method comprising:

causing the cavitation in the liquid substance behind an obstacle by installing the obstacle in a flow passage for the liquid substance to which a flow speed is imparted; and generating the plasma with the plasma generation mechanism.

4. A liquid substance sterilizing apparatus comprising:

a suction stirring pump that suctions a liquid substance to be sterilized under a negative pressure with a negative-pressure suction force generated by rotation of a rotary blade and causes cavitation by stirring the liquid substance subjected to the suction under the negative pressure with the rotary blade; and a plasma generation mechanism that generates plasma in air bubbles generated in the liquid substance by the cavitation.

5. The liquid substance sterilization apparatus according to claim 4, wherein the suction stirring pump includes a throttle flow passage that allows the liquid substance, to which a flow speed is imparted by performing stirring with the rotary blade, to pass therethrough.

6. The liquid substance sterilizing apparatus according to claim 4, wherein the plasma generation mechanism is provided in a discharge pipe that is connected to the suction stirring pump and allows the liquid substance to be discharged therethrough.

7. The liquid substance sterilizing apparatus according to claim 4, further comprising:

a circulation flow passage that allows the liquid substance discharged from the suction stirring pump to be circulated to the suction stirring pump.

8. A liquid substance sterilizing apparatus comprising:

a flow speed imparting mechanism that imparts a flow speed to a liquid substance to be sterilized;

an obstacle that is installed in a flow passage for the liquid substance to which the flow speed is imparted by the flow speed imparting mechanism, thereby causing cavitation in the liquid substance to which the flow speed is imparted; and a plasma generation mechanism that generates plasma in air bubbles generated in the liquid substance by the cavitation.

9. The liquid substance sterilizing apparatus according to claim 8, wherein the obstacle is an electrode of the plasma generation mechanism.

10. The liquid substance sterilizing apparatus according to claim 8, wherein the obstacle is an obstacle installed on an upstream side of an electrode of the plasma generation mechanism.

* * * * *